US00RE40931E

(19) United States
(12) Reissued Patent
Khachik

(10) Patent Number: US RE40,931 E
(45) Date of Reissued Patent: Oct. 6, 2009

(54) PROCESS FOR ISOLATION, PURIFICATION, AND RECRYSTALLIZATION OF LUTEIN FROM SAPONIFIED MARIGOLD OLEORESIN AND USES THEREOF

(75) Inventor: Frederick Khachik, Rockville, MD (US)

(73) Assignee: The Catholic University of America, Washington, DC (US)

(21) Appl. No.: 11/330,423

(22) Filed: Jan. 10, 2006

Related U.S. Patent Documents

Reissue of:
(64) Patent No.: 5,382,714
Issued: Jan. 17, 1995
Appl. No.: 08/210,009
Filed: Mar. 17, 1994

(51) Int. Cl.
*C07C 35/08* (2006.01)
*C07C 35/18* (2006.01)

(52) U.S. Cl. ..... 568/834; 568/816; 568/822; 568/823; 568/824; 568/832; 568/834; 568/810; 568/819; 568/700; 568/913; 435/67; 426/540; 426/310

(58) Field of Classification Search ..... 568/816, 568/834, 822, 823, 824, 832, 810, 819, 700, 568/913; 435/67; 426/540, 310
See application file for complete search history.

(56) References Cited

U.S. PATENT DOCUMENTS

| | | | |
|---|---|---|---|
| 2,527,602 | A | 10/1950 | Wall |
| 3,248,301 | A | 4/1966 | Burdick |
| 3,274,072 | A | 9/1966 | Burdick |
| 3,523,138 | A | 8/1970 | Grant |
| 3,732,214 | A | 5/1973 | Surmatis et al. |
| 3,879,424 | A | 4/1975 | Surmatis et al. |
| 4,028,217 | A | 6/1977 | Okada et al. |
| 4,048,203 | A | 9/1977 | Philip |
| 4,316,917 | A | 2/1982 | Antoshkiw et al. |
| 4,851,339 | A | 7/1989 | Hills |
| 4,871,551 | A | 10/1989 | Spencer |
| 5,019,668 | A | 5/1991 | Keat et al. |
| 5,602,286 | A | 2/1997 | Muralidhara |
| 6,743,953 | B2 | 6/2004 | Kumar et al. |

FOREIGN PATENT DOCUMENTS

| | | |
|---|---|---|
| JP | 0096032 | 6/1983 |

OTHER PUBLICATIONS

Kuzmicky, et al., Pigmentation Potency of Xanthophyll Sources, Poultry Science, Mar. 1968, pp. 389–397, vol. XLVII, No. 2.

Tyczkowski, et al., Preparation of Purified Lutein and Its Diesters from Extracts of Marigold (Tagetes erecta), Department of Poultry Science, North Carolina University, Aug. 2, 1990, pp. 651–654, vol. 70.

The Merck Index, 9$^{th}$ Edition, p. 1298, 1976.

Karrer et al., Helvetica, Chimica, Acta, vol. 30, pp. 531–535, 1947.

Karrer, Chemical Abstracts, vol. 41, No. 13, 4141f, Jul. 1947.

*Primary Examiner*—Elvis O Price
(74) *Attorney, Agent, or Firm*—Husch Blackwell Sanders LLP

(57) ABSTRACT

A method of isolating, purifying and recrystallizing substantially pure lutein, preferably from saponified marigold oleoresin in its pure free form, apart from chemical impurities and other carotenoids. Lutein may be used as an analytical standard or in cancer prevention trials and as a safe and effective color additive for human food.

1 Claim, No Drawings

PROCESS FOR ISOLATION, PURIFICATION, AND RECRYSTALLIZATION OF LUTEIN FROM SAPONIFIED MARIGOLD OLEORESIN AND USES THEREOF

Matter enclosed in heavy brackets [ ] appears in the original patent but forms no part of this reissue specification; matter printed in italics indicates the additions made by reissue.

*NOTICE More than one reissue application has been filed for the reissue of U.S. Pat. No. 5,382,714. The reissue applications are the present reissue application and reissue patent application Ser. No. 11/150,599, both of which are reissues of U.S. Pat. No. 5,382,714.*

BACKGROUND OF THE INVENTION

Lutein is a naturally occurring carotenoid that has no vitamin A activity. There are three asymmetric centers in lutein at C-3, C-3', and C-6' positions. The absolute configuration of lutein in foods (fruits and vegetables) and human serum/plasma is known to be 3R,3'R,6'R. This configurational isomer of lutein which is the most abundant form of lutein is also known as lutein A. However in human serum/plasma a small amount of another configurational isomer of lutein, namely (3R,3'S,6'R)-lutein also known as 3'-epilutein or lutein B has been shown to be present. The chemical structures of lutein and 3'-epilutein are shown below. Other known configurational isomers of lutein have only been isolated from the integument of marine fishes.

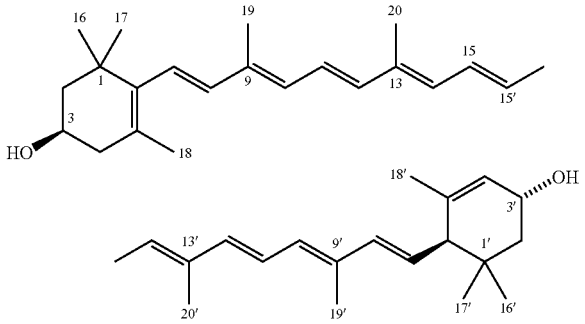

(3R,3′R,6′R)-β,ε-Carotene-3,3′-diol (Lutein)

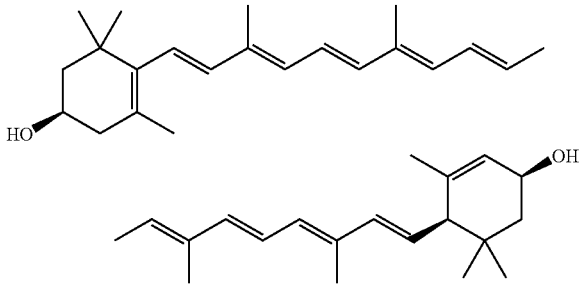

(3R,3′S,6′R)-β,ε-Carotene-3,3′-diol (3′-Epilutein)

The terms all-E- and Z-isomers are new terminology used for lutein and other carotenoids, and refer to old terminology of all-trans and cis isomers of these compounds, respectively. Unless specified lutein refers to all-E (all-trans) isomer.

Numerous epidemiological studies in various populations have shown that the consumption of substantial amounts of fruits and vegetables reduce the risk of cancer. One hypothesis is that the carotenoids in these foods act as antioxidants through a free radical mechanism by quenching singlet oxygen and other oxidizing species resulting in the termination of free radical chain reactions and in the prevention of cellular oxidative damage. The correlation between dietary carotenoids and carotenoids found in human serum or plasma indicate that only selected groups of carotenoids make their way into the human bloodstream to exert their effect. To date, 19 carotenoids have been identified to be present in human blood. With the exception of β-carotene, none of these carotenoids have been studied for their anti-cancer activity.

There has been recent evidence to suggest that lutein, one of the most abundant carotenoids in the diet and in human blood possesses strong antioxidant capabilities and may be useful in reduction of the incidence of cancer. The allylic hydroxyl group at the C-3' position of the E-end group of this compound can readily undergo oxidation as a result of activation by the neighboring double bond. The non-allylic hydroxyl group at the C-3 position of the β-end group can also activate the C-4 carbon allylic to the double bond making this carbon highly susceptible to direct oxidation. These oxidation reactions result in the formation of four metabolites of lutein, which have been isolated and characterized from extracts of human serum or plasma. Further evidence for an in vivo oxidation of lutein has also been obtained in human feeding studies. To date, pure lutein suitable for human use has not been commercially available for use as a chemopreventive agent in clinical trials. Pure lutein, free from chemical contaminants and suitable for human consumption, is needed to design and conduct proper human intervention studies.

Lutein is one of the major constituents of green vegetables and fruits such as broccoli, green beans, green peas, lima beans, Brussels sprouts, cabbage, kale, spinach, lettuce, kiwi, and honeydew. The lutein in these green vegetables and fruits exists naturally in the free non-esterified form and co-exists with other carotenoids.

However, the isolation and purification of free form, pure lutein in large quantities from green vegetables is not economical. Many expensive and time-consuming purification steps are required to remove and purify lutein from the large quantities of chlorophylls, β-carotene, and carotenoids epoxides that are also present in green vegetables.

Lutein is also abundant in a number of yellow/orange fruits and vegetables such as mango, papaya, peaches, prunes, acorn squash, winter squash, and oranges. Lutein in these yellow/orange fruits and vegetables exists in the esterified form with fatty acids such as myristic, lauric, and palmitic acids. Upon ingestion of these foods, lutein esters undergo hydrolysis to regenerate free lutein which is then absorbed and metabolized by the body. However, these yellow/orange fruits and vegetables also contain high concentrations of a number of other carotenoids which make the isolation and purification of lutein costly and time-consuming.

Marigold flower petals are an excellent source of lutein because they contain high levels of lutein and no significant levels of other carotenoids. Extracts of marigold flowers are commercially available but consist of lutein that is esterified with fatty acids such as lauric, myristic, and palmitic acids. Lutein in its natural form as it exists in marigold flowers does not exist as free lutein. Upon saponification of the marigold extract, the lutein fatty acid esters are converted to lutein. However, the resulting lutein is still contaminated with a number of chemical impurities. To date, no method has been described to isolate and purify the free form of lutein from these chemical impurities.

The saponified extracts of marigold flower petals are commercially available and currently used in chicken feed to enhance the yellow color of egg yolk and the skin of chickens. However, the extract is not acceptable as a direct color additive for human foods because of the presence of impurities. The availability of substantially pure lutein suitable for human use and the evidence that significant levels of lutein derivatives are normally found in human blood would also make lutein an attractive color additive.

While chemical processes for synthesis of lutein from commercially available starting materials are known, such processes are extremely time-consuming, involve multiple steps, and to date have simply not provided an economical process for production of lutein. It therefore appears that the most likely economic route to substantially pure lutein is through a process that extracts, isolates, and purifies lutein from marigold flowers. Such substantially pure lutein, if economically available, could be used in cancer prevention studies, as well as an attractive, naturally-occurring, non-harmful color additive in human foods.

It is therefore evident that there is a need for a carotenoid composition of substantially pure lutein. The primary objective of the present invention is the fulfillment of this need.

Another objective of the present invention is to provide a method for isolating, purifying and recrystallizing lutein in high purity from a saponified marigold extract.

Another objective of the present invention is to provide a method for isolating, purifying and recrystallizing lutein in high purity which is economical to perform with a minimum of processing steps.

Another objective of the present invention is to provide purified lutein in crystalline form such that it is acceptable for human consumption and use in cancer prevention trials and treatments without causing toxic side effects due to residual impurities.

Yet a further objective of the present invention is to provide purified lutein in crystalline form such that it is acceptable as a color additive in human foods.

The method and means of accomplishing each of the above objectives as well as others will become apparent from the detailed description of the invention which follows hereinafter.

SUMMARY OF THE INVENTION

The present invention relates to an efficient method of isolating, purifying, and recrystallizing substantially pure lutein preferably from a saponified marigold oleoresin. Lutein purified according to this method is free from a number of chemical impurities that are known constituents of flowers and plants. Lutein, in pure form may be used as an analytical standard and in cancer prevention trials, and as a safe and effective color additive in human food. The method involves purifying, preferably, a saponified marigold extract through use of a series of filtrations and water/alcohol washes to obtain crude lutein crystals. The crystals are dissolved in a halogenated organic solvent in which lutein is strongly soluble and then a second organic solvent in which lutein is only partially soluble. Upon cooling of the mixture Lutein is recrystallized in a high purity and then filtered and dried under vacuum.

DETAILED DESCRIPTION OF THE INVENTION

A saponified marigold oleoresin commercially available under the trademark "Kemin Yellow Oil" from Kemin Industries, Inc., Des Moines, Iowa, is a preferred starting material. While other extracts of marigold flowers may be used, this particular one from marigold petals is most preferred because it is substantially free from other carotenoids. Generally, the concentration of other carotenoids in the starting material should be 10% or less. The starting material, preferably the marigold petal extract available as "Kemin Yellow Oil" is homogenized with a mixture of distilled water and ethanol, preferably at 5° C.–10° C. for about 30 minutes to remove water soluble impurities such as anthocyanins (typical red pigments found in extracts from flowers). The ratio of distilled water to alcohol should be from 3 to 1, preferably 2.3 to 1.

The saponified marigold oleoresin is derived from an organic solvent extraction of dried marigold flowers (Tagetes erecta) and then treated with an alkaline solution resulting in lutein free from fatty acids such as palmitic, myristic and lauric acids. At the preferred ratio of water/ethanol of 2.3:1 (within the range of from 3 to 1) and at the cold temperature employed, lutein precipitates out from saponified marigold oleoresin as orange crystals which are collected upon filtration. Other ratios of water/alcohol not within the range specified resulted in lower recoveries of lutein. The filtrate contains potassium hydroxide (from the previous saponification step of marigold extract employed by the manufacturer of the starting material.), anthocyanins, and water soluble flavonoids.

Instead of ethanol, other alcohols such as methanol or isopropyl alcohol may also be employed. However, since the purified lutein is required not to contain even traces of any toxic chemicals, the use of methanol instead of food grade ethanol in this purification process is not normally recommended.

The cold temperatures of 5° C.–10° C. result in the best recoveries for lutein, since this compound is not very well soluble in cold alcohol solutions. At higher temperatures, however, solubility of lutein in alcohol is increased which of source results in lower yields for this compound. Temperatures within the above range provide economical yields.

The retained orange precipitate of lutein is then washed with distilled water until the filtrate is almost colorless and the pH is near neutral. This ensures the complete removal of anthocyanins (red pigment) and the potassium hydroxide from the precipitated lutein.

The precipitate is then washed sequentially with cold (0° C.–5° C.) alcohol, preferably ethanol and then preferably with hexane. These sequential washes result in the removal of the plant sterols and the final wash with hexane also results in removal of alcohol from lutein. As a result the crystals of this compound are dried at a faster rate due to the evaporation of the volatile hexane. The hexane wash also removes most of α- and β-cryptoxanthin, and particularly β-carotene which are present in very low concentrations in the saponified marigold extract.

Instead of hexane, other straight chain hydrocarbons such as pentane, heptane, or petroleum ether (b.p.=30° C.–60° C.) can also be effectively used since lutein has very low solubility in all of these organic solvents. The resulting orange crystals of lutein obtained at this point are normally about 70% pure as determined spectrophotometrically. While 70% pure lutein may be acceptable for use in animal feed, further purification of this compound may be employed to produce lutein with purity greater than [97%] *90%* for human consumption.

Final purification of lutein is accomplished by recrystallization from a binary solvent system, preferably a 1:1 mixture of dichloromethane and hexane. This binary solvent system has never been used in the purification of lutein. The choice of dichloromethane is because of the excellent solubility of lutein in this solvent. Instead of dichloromethane other halogenated solvents such as chloroform or 1, 2-dichloroethane can also be used; and instead of hexane one can also use other straight chain hydrocarbons such as pentane, heptane, and petroleum ether (b.p. 30°–60° C.). Therefore, partially purified lutein (70% pure) is dissolved in a minimum amount of dichloromethane preferably containing 1% triethylamine and hexane is added until the solution becomes cloudy. The 1% addition of triethylamine to dichloromethane neutralizes the trace amount of the acids that are normally present in halogenated solvents. These residual acids could result in conversion of lutein to another carotenoid known as 2', 3'-anhydrolutein. Thus, the 1% addition of triethylamine is preferred to prevent lutein from undergoing side reactions and to maximize the yield of pure lutein.

The above cloudy solution is kept within the range of from −20° C. to −10° C. to commence recrystallization. At this range of temperature, the recrystallization is most efficient and it is usually completed within 2 to 3 hours. Storage of the solution at 0° C. prolongs the recrystallization process which may take as long as 24 hours and the recovery of pure lutein is not optimum. The crystals of lutein are then filtered off and washed, preferably with cold (0° C.) hexane. The pure crystalline lutein is dried in vacuo, i.e., at 50° C. for three days.

The purity of the resulting lutein is usually greater than 90%, most often greater than 97% as determined by UV/visible spectrophotometry. Based on quantitative HPLC analysis, the purified lutein consists of 94.79% lutein, 3.03% of its geometrical isomers, and a total of 2.18% of 2', 3'-anhydrolutein, zeaxanthin, α-cryptoxanthin, and β-cryptoxanthin. The presence of the low levels of these carotenoids is not of any concern since these carotenoids are of dietary origin and are found routinely at much higher concentrations relative to that of lutein in human serum or plasma. NMR analysis showed no residual solvents (i.e., dichloromethane, hexane, ethanol, triethylamine) or other non-carotenoid impurities. The lutein purified according to this method exists in substantially purer form in comparison with lutein found in the matrix of any naturally occurring plant. In comparison with multi-step chemical synthesis, the purification of lutein according to this method is much more economical. Furthermore, lutein isolated and purified from marigold flowers does not contain hazardous chemical impurities as a result of various organic reagents that are normally employed in the sequential synthesis of this compound.

The following examples are offered to illustrate but not limit the product and process of the present invention.

EXAMPLES

Example 1

Saponified marigold oleoresin available commercially as "Kemin Yellow Oil" was obtained. It was previously processed in the following manner.

Upon receipt the flowers were tested for herbicides and pesticides in order to ensure that they meet qualifications for food ingredients. The completed oleoresin extract (200 g) was then subjected to saponification with aqueous potassium hydroxide. This was accomplished through continuous mixing under heat (65°–70° C.) of food grade aqueous potassium hydroxide (45%) and the oleoresin until greater than 98% of lutein was free from fatty acid esters. The saponification was normally completed within 35 minutes. The product was then homogenized with a mixture of distilled water (700 mL)/ethanol (300 mL, food grade):2.3/1 at room temperature for 30 minutes. The mixture was filtered off and the filtrate was discarded. The retained orange precipitate of lutein was washed with distilled water until the filtrate was almost colorless and the pH was neutral. The precipitate was then washed sequentially with cold (0° C.–5° C.) ethanol (200 mL) and hexane (200 mL), respectively. The resulting lutein obtained as orange crystals from three to be 70% pure by spectrophotometric analysis.

Final purification was accomplished by recrystallization from a 1:1 mixture of dichloromethane and hexane by dissolving the 70% pure crystals in about 550 ml of dichloromethane containing 1% of triethylamine. The hexane was added until the solution became cloudy. The cloudy solution was kept at −20° C. to −10° C. to commence recrystallization. This was completed within about 3 hours resulting in orange crystals of lutein. The crystals were then filtered off and washed with cold (0° C.) hexane (200 ml) and dried in vacuo at 50° C. for 3 days. The purity of lutein in this instance was greater than 97%.

Example 2

Saponified marigold oleoresin (200 g) was homogenized with a mixture of distilled water/ethanol (food grade) at various ratios of 0° C.–10° C. for 30 minutes. The mixture was filtered off and the filtrate was discarded. The retained orange precipitate of lutein was washed with distilled water until the filtrate was almost colorless and the pH was neutral. The precipitate was then washed sequentially with cold (0° C.–5° C.) ethanol (200 mL) and hexane (200 mL), respectively. The yield of lutein obtained as orange crystals from three experiments employing different ratios of water/ethanol are shown below. The lutein obtained in all three experiments was shown to be about 70% pure by spectrophotometric analysis.

| Ratio of Water/Ethanol | Weight (g) of Crude Lutein Isolated from 200 g Saponified Marigold Oleoresin |
|---|---|
| 2.3/1 | 28 |
| 3.0/1 | 22 |
| 1.0/2 | 15 |

This example demonstrates the highest yield of lutein is obtained with 2.3/1 ratio of water/ethanol. The final purification step by recrystallization was accomplished as in Example 1, to give lutein in excess of 97% purity.

The purity and the constituents of the lutein isolated from "Kemin Yellow Oil" have been determined by UV/visible spectrophotometry as well as high performance liquid chromatography-photodiode array detection/mass spectrometry (HPLC/MS). In addition proton nuclear magnetic resonance (NMR) spectrum of the purified lutein has been obtained in order to determine the presence of trace amounts of residual solvents and other impurities.

UV/Visible Spectrophotometric Analysis: The purity of lutein is greater than 97% as determined from the absorption spectrum of this compound in ethanol, which exhibits maxima at 422, 446, and 476 nm and extinction coefficient of 1% E=2550 in ethanol at 446 nm.

HPLC/MS Analysis: The purified lutein has been examined by HPLC equipped with a photodiode array detector on both a $C_{18}$-reversed phase column and a silica-based nitrile bonded column. The HPLC system was interfaced with a Hewlett-Packard particle beam mass spectrometer. The analysis of the purified lutein with HPLC/MS system in addition to HPLC peak purity determination at various wavelengths also provided further evidence for purity of this compound from the total ion chromatogram obtained by mass spectrometry analysis.

The HPLC profile of the purified lutein on a $C_{18}$-reversed phase column was observed. 1). As revealed in chromatograms, the purified lutein also contains four other carotenoids as minor impurities. In the order of chromatographic elution on a $C_{18}$-reversed phase column, the carotenoids in the purified and recrystallized lutein are: lutein+zeaxanthin (coeluting HPLC peaks, 99.31%), 2', 3'-anhydrolutein (0.23%), α-cryptoxanthin (0.34%), and β-cryptoxanthin (0.10%). Since lutein and its geometrical isomers as well as zeaxanthin (present as a minor component) are not separated on the $C_{18}$-reversed phase column, a nitrile bonded column was employed. The HPLC profile of the purified lutein on the nitrile bonded column revealed that under these chromatographic conditions 2', 3'-anhydrolutein, α-cryptoxanthin, and β-cryptoxanthin appear as one HPLC peak, while lutein and zeaxanthin and several of their geometrical isomers are well separated. Based on Quantitative HPLC analysis of purified lutein on $C_{18}$-reversed phase and nitrile bonded columns, the chemical composition of this compound isolated and purified from extracts of marigold flowers are shown in Table I.

TABLE I

Carotenoid Composition of Lutein Isolated and Purified from Extracts of Marigold Flowers (*Tagetes erecta*, variety orangeade)

| Carotenoids | Composition (%) |
|---|---|
| all-E Lutein | 94.79 |
| 9Z-Lutein | 0.14 |
| 9"Z-Lutein | 0.15 |
| 13 + 13'Z-Lutein | 0.29 |
| Poly Z-Lutein | 2.45 |
| Total of Lutein + Z-Isomers | 97.82 |
| 2',3'-Anhydrolutein | 0.23 |
| All-E-Zeaxanthin | 1.51 |
| α-Cryptoxanthin | 0.34 |
| β-Cryptoxanthin | 0.10 |
| Total of Other Carotenoids | 2.18 |

From these data it appears that the purified lutein from marigold flowers consists of 94.79% of all E-lutein, 3.03% of its geometrical isomers (Z-luteins), and a total of 2.18% of 2', 3'-anhydrolutein, zeaxanthin, α-Cryptoxanthin, and β-Cryptoxanthin. The presence of the low levels of these carotenoids in the purified lutein product should not be of any concern since these carotenoids are of dietary origin and they are found routinely at much higher concentrations relative to that of lutein in human serum/plasma. Individual carotenoids separated by the two HPLC columns described above have also been characterized from comparison of their absorption and mass spectra determined by a photodiode array detector interfaced into a mass spectrometer with those of standards characterized previously.

NMR Analysis: The proton NMR spectrum of the purified lutein was in agreement with the spectrum of this compound reported previously and no residual solvents (i.e., dichloromethane, hexane, methanol, triethylamine) or other non-carotenoid impurities (plant sterols and fatty acids) could be detected in this sample.

No substantially pure form of lutein derived from plant extract having these levels of purity has heretofore been available.

Example 3

Preparation of Lutein Dose For Oral Supplementation

Carotenoids are considered among the fat soluble nutrients and are usually associated with the lipoprotein fractions of human blood. Therefore, the absorption and bioavailability of carotenoids is significantly increased if these compounds are orally ingested with a small amount of an oil or foods that contain certain amounts of lipids. In a human study that was conducted the following preparation of lutein resulted in excellent absorption of this compound by the subjects as determined from the analysis of their plasma carotenoid profile. In the following, the procedure employed for the preparation of a small batch (100 dose, each 10 mg) of purified lutein is described.

Purified lutein from marigold flowers extract (1 g) was added to absolute alcohol (75 mL). To this solution α-tocopherol (50 mg) and food grade polysorbate 80 (an emulsifier, 4 g) was added and the mixture was sonicated for 10 minutes. The addition of α-tocopherol (0.01% by weight) was to stabilize lutein and prevent this compound from possible oxidation during long term storage. The above suspension was then mixed with 350 g of light and mild olive oil (saturated fat/polyunsaturated fat=2/1) and the mixture was sonicated for 5 minutes. This resulted in a suspension of lutein in olive oil which was stored under nitrogen in a refrigerator. 7 mL aliquots of this suspension was shown by spectrophotometric analysis to contain 10 mg of lutein. At various intervals, the stability and the purity of lutein suspension in the olive oil was determined by spectrophotometric and HPLC analysis. The stability studies revealed that lutein prepared and stored under the conditions described above is stable for up to one month. In one study each 7 mL aliquot of the olive oil (containing 10 mg lutein) was spread on a bagel prior to ingestion. Alternatively, this small volume of oil can be readily taken with other foods. Although this preparation of lutein dose is appropriate for conducting human studies with a limited number of subjects, other preparations of this compound into tablets or capsules can be accomplished. The formulation of β-carotene into tablets and capsules which has been developed by Hoffmann-La Roche Inc. (Nutley, N.J.), may also be found suitable for lutein with some minor modifications.

From the above examples it can be seen that applicant has prepared the first ever substantially pure lutein as derived initially from plant extracts. The product is substantially free of impurities, substantially free of other carotenoids, and contains only very low levels of certain carotenoids of dietary origin. The presence of these carotenoids are of no concern since they are found routinely at much higher concentrations in human serum/plasma relative to that of lutein.

It can therefore be seen that the invention accomplishes at least all of its stated objectives.

What is claimed is:

[1. The carotenoid composition consisting essentially of substantially pure lutein crystals derived from plant extracts that contain lutein, said lutein crystals being of the formula:

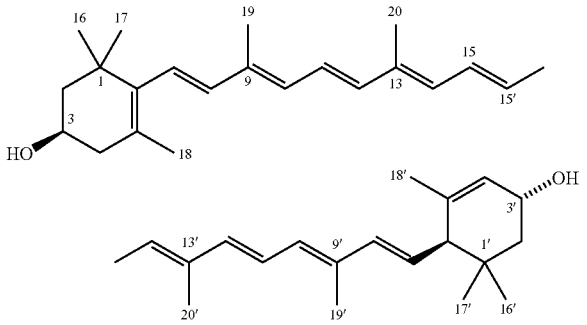

(3R,3′R,6′R)-β,ε-Carotene-3,3′-diol (Lutein)

wherein the lutein is substantially free from other carotenoids and chemical impurities found in the natural form of lutein in the plant extract.]

[2. The lutein carotenoid composition of claim 1 wherein the plant extract is derived from naturally occurring plants selected from the group consisting of fruits, vegetables and marigolds.]

[3. The lutein carotenoid composition of claim 1 admixed with an edible triglyceride oil to provide a dose form.]

[4. The lutein carotenoid composition of claim 1 wherein the lutein is derived from marigold flower extract.]

[5. A method of obtaining substantially pure, free form lutein crystals from saponified marigold extract, comprising the steps of:

(a) mixing the marigold extract with water/alcohol mixture remove soluble impurities;

(b) lowering the temperature of the mixture to a temperature to precipitate lutein crystals;

(c) washing the lutein crystals with water to remove water soluble impurities;

(d) washing the lutein crystals with an organic solvent mixture to remove organic impurities, and thereafter recrystallizing the lutein.]

[6. The process of claim 5 wherein the recrystallization involves dissolving the lutein crystals in a binary solvent system and thereafter lowering the temperature to recrystallize lutein in substantially pure form free from other carotenoids and chemical impurities.]

[7. The process of claim 6 wherein the binary solvent system is a halogenated organic solvent in which lutein is strongly soluble followed by addition of a second organic solvent in which lutein is only partially soluble.]

[8. The method of claim 7 wherein the halogenated solvent is dichloromethane, chloroform, or 1, 2-dichloroethane.]

[9. The method of claim 8 wherein the halogenated solvent contains a small but effective amount of an organic base to neutralize trace amounts of acids that are normally present in halogenated solvents.]

[10. The process of claim 9 wherein the organic base is triethylamine.]

[11. The process of claim 10 wherein triethylamine is present at about 1% by volume of the added halogenated solvent.]

[12. The process of claim 7 wherein the organic solvent is a straight chain hydrocarbon.]

[13. The method of claim 5 wherein the ratio of water to alcohol is 2.3 to 1 in step (a).]

[14. The method of claim 5 wherein the alcohol in step (a) is selected from the group consisting of ethanol, methanol and isopropyl alcohol.]

[15. The method of claim 6 wherein the temperature is lowered within the range of from about 5° C. to about 10° C.]

[16. The method of claim 5 wherein the organic solvent mixture in step (d) includes a straight chain hydrocarbon solvent and an alcohol.]

[17. The method of claim 16 wherein the temperature of the alcohol and the organic solvent is from about 0° C. to about 5° C.]

[18. The method of claim 7 wherein the ratio of the halogenated organic solvent and the second organic solvent is 1:1.]

[19. The method of claim 6 wherein the temperature of the solution is lowered to within the range of from −20° C. to −10° C. for from 2 to about 3 hours.]

[20. The method of claim 6 wherein the recrystallized lutein is dried in vacuo at 50° C. for 3 days.]

*21. A method for providing lutein to humans which comprises:*

*(a) providing a lutein composition suitable for human consumption having (1) at least about 90% lutein having been extracted and purified from plant extracts which contain 10% or less of non-lutein carotenoids, (2) no traces of toxic chemicals that would render the lutein composition unsuitable for human consumption and (3) significantly less than about 10% of non-lutein carotenoids obtained by purification of said plant extracts; and*

*(b) administering said lutein composition to a human.*

* * * * *